United States Patent [19]

Ong et al.

[11] 4,198,417

[45] Apr. 15, 1980

[54] PHENOXYPHENYLPIPERIDINES

[75] Inventors: Helen H. Ong, Whippany; James A. Profitt, Somerville, both of N.J.

[73] Assignee: American Hoechst Corporation, Bridgewater, N.J.

[21] Appl. No.: 2,346

[22] Filed: Jan. 10, 1979

[51] Int. Cl.² ............... A61K 31/445; C07D 211/64
[52] U.S. Cl. ............................ 424/267; 546/207; 546/214; 546/215; 546/226; 546/225; 546/228
[58] Field of Search ............... 546/207, 214, 215, 225, 546/226, 228; 424/267

[56] References Cited

U.S. PATENT DOCUMENTS 4,066,654    1/1978    Adelstein et al. ................ 546/228

*Primary Examiner*—Alan L. Rotman
*Assistant Examiner*—Robert T. Bond
*Attorney, Agent, or Firm*—Curtis, Morris & Safford

[57] ABSTRACT

Novel phenoxyphenylpiperidines and methods of preparing same are described. These compounds are useful as analgetics, antidepressants, anticonvulsants and intermediates for preparing other pharmaceutically active compounds.

74 Claims, No Drawings

PHENOXYPHENYLPIPERIDINES

This invention relates to novel phenoxyphenylpiperidines which are useful as analgetics, antidepressants and anticonvulsants, to methods of treatment with pharmaceutically effective amounts thereof and to pharmaceutical compositions containing such compounds as essential active ingredients. Additionally, some compounds of this invention are useful as intermediates in the preparation of more active compounds of this invention and other pharmaceutically active compounds described in our application filed on even date herewith and entitled "Spiro[dibenz(b,f)oxepinpiperidine]s."

The phenoxyphenylpiperidines of the invention have the formula

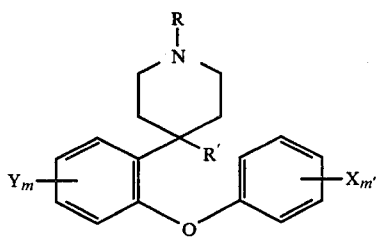

in which R is hydrogen, loweralkyl, loweralkenyl, loweralkynyl, cycloalkylloweralkyl, phenylloweralkyl, loweralkanoyl, phenoxycarbonyl, aminocarbonyl, benzoylloweralkyl, cyano, ethylene glycol ketal of the formula

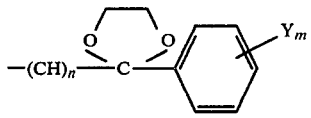

and tetrahydrofurylmethyl; R' ic cyano, COOH, COZ, loweralkylcarbonyl or loweralkoxycarbonyl; X and Y are the same or different and each can be hydrogen, chlorine, fluorine, bromine, methoxy, methylthio or trifluoromethyl; Z is chlorine, fluorine or bromine; m and m' are the same or different and each can be the integer 1 or 2; n is an integer of 1 to 4, inclusive, and a pharmaceutically acceptable acid addition salt thereof.

In the above definitions and throughout, the following have the assigned significance, unless otherwise specified:

"lower" means the particular group described thereby contains up to and including 5 carbon atoms and can be straight or branched chain;

"ambient" means the temperature is that of its natural surroundings, i.e., room temperature or about 15°–30° C.

"cycloalkyl" contains between 3 and 7, inclusive, carbon atoms;

"phenyl" or "phenyl derivative" (e.g. benzoyl) means the particular phenyl ring can contain one or more of the following: nitro, amino, chlorine, fluorine, bromine, methoxy, loweralkyl or trifluoromethyl.

Acids useful for preparing the pharmaceutically acceptable acid addition salts of the present invention include inorganic acids such as hydrochloride, hydrobromic, sulfuric, nitric, phosphoric and perchloric acids, as well as organic acids such as tartaric, citric, acetic, succinic, maleic, fumaric and oxalic.

To the best of our knowledge, the compounds of the present invention have not heretofore been described or suggested.

The compounds of the present invention are useful as analgetics due to their ability to alleviate pain in mammals, as demonstrated in the phenyl-2-quinone writhing assay in mice, a standard assay for analgesia [Proc. Soc. Exptl. Biol. Med., 95, 729 (1957)]. Tabulated below are the percentages of inhibition of writhing accomplished with various subcutaneous dosages of representative compounds of the invention.

| Compound | Dose Mg/Kg | % Inhibition |
|---|---|---|
| 4-acetyl-1-methyl-4-(2-phenoxyphenyl)-piperidine oxalate | 1.9 | 50 |
| 4-cyano-1-methyl-4-(2-phenoxyphenyl)-piperidine hydrochloride | 3.8 | 50 |
| 1-cyclopropylmethyl-4-ethylcarbonyl-4-(2-phenoxyphenyl)piperidine oxalate | 4.4 | 50 |
| 4-ethoxycarbonyl-4-(2-phenoxyphenyl)-piperidine oxalate | 6.6 | 50 |
| 4-ethylcarbonyl-1-methyl-4-(2-phenoxyphenyl)piperidine oxalate | 7.3 | 50 |
| 1-cyclopropylmethyl-4-ethoxycarbonyl-4-(2-phenoxyphenyl)piperidine hydrobromide | 11.9 | 50 |
| 1-methyl-4-(2-phenoxyphenyl)-4-propylcarbonyl-piperidine oxalate | 25 | 79 |
| 4-ethylcarbonyl-1-phenethyl-4-(2-phenoxyphenyl)piperidine hydrobromide | 25 | 67 |
| 4-ethoxycarbonyl-1-methyl-4-(2-phenoxyphenyl)piperidine hydrobromide | 25 | 65 |

For comparison, aspirin and propoxyphene, known analgesic agents, effect a 34% and 50% inhibition at a dose of 60 mg/kg and 28 mg/kg, respectively. These date illustrate that the compounds of this invention are useful for alleviating pain in mammals when administered in amounts ranging from about 0.1 to about 100 mg/kg of body weight per day.

Compounds of the present invention are also useful for the treatment of depression in mammals, as demonstrated by their ability to inhibit tetrabenazine induced depression in mice [International Journal of Neuropharmacology, 8, 73 (1969)], a standard assay for useful antidepressant properties. Tabulated below are the various intraperitoneal dosages of representative compounds of the invention which effected a 50% inhibition of the ptosis of tetrabenazine induced depression in test mice.

| Compound | Dose Mg/Kg |
|---|---|
| 1-cyclopropylmethyl-4-ethoxycarbonyl-4-(2-phenoxyphenyl)piperidine hydrobromide | 7.2 |
| 1-methyl-4-(2-phenoxyphenyl)-4-propylcarbonylpiperidine oxalate | 9.6 |
| 1-cyclopropylmethyl-4-ethylcarbonyl-4-(2-phenoxyphenyl)piperidine oxalate | 11.8 |
| 4-acetyl-1-methyl-4-(2-phenoxyphenyl)piperidine oxalate | 19.0 |

These data illustrate that compounds of the invention are useful for the treatment of depression in mammals when administered in amounts ranging from about 0.1 to about 100 mg/kg of body weight per day.

Compounds of the present invention are further useful as anticonvulsant agents for mammals, as determined by the method of Woodbury, L. A. and Davenport, V. D. [Arch., Int. Pharmacodynam, 92, pp 97–107 (1952)]. Tabulated below are the various intraperitoneal dosages of representative compounds of the invention which effected a 50% protection from the effect of supramaximal electro shock.

| Compound | Dose Mg/Kg |
| --- | --- |
| 4-acetyl-1-methyl-4-(2-phenoxyphenyl)piperidine oxalate | 25 |
| 1-cyclopropylmethyl-4-ethylcarbonyl-4-(2-phenoxyphenyl)piperidine oxalate | 26 |
| 4-cyano-1-methyl-4-(2-phenoxyphenyl)piperidine hydrochloride | 31 |
| 4-acetyl-1-cyclopropylmethyl-4-(2-phenoxyphenyl)-piperidine oxalate | 25* |

*produced a 67% protection

These data illustrate that compounds of the invention are useful in treating convulsions in mammals when administered in amounts ranging from 0.1 to about 100 mg/kg of body weight per day.

Compounds of this invention include:
1-ethyl-4-ethylcarbonyl-4-(2-phenoxyphenyl)piperidine;
4-acetyl-1-ethyl-4-(2-phenoxyphenyl)piperidine;
1-methyl-4-[2-(2-trifluoromethylphenoxyphenyl)-piperidine-4-carboxylic acid;
4-acetyl-1-cyclohexylmethyl-4-(2-phenoxyphenyl)-piperidine;
4-[2-(3,4-dichlorophenoxy)phenyl]-4-cyanopiperidine;
4-acetyl-4-[2-(4,6-dibromo-5-fluorophenoxy)phenyl]-piperidine;
4-[2-(4-bromo-5,6-dichlorophenoxy)phenyl]-4-ethylcarbonylpiperidine;
4-[2-(3,4-dichloro-5-trifluoromethylphenoxy)-phenyl]-1,4-dicyanopiperidine;
4-acetyl-1-[4-(4-fluorobenzoyl)-n-butyl]-4-(2-phenoxyphenyl)piperidine;
4-acetyl-1-[2-(4-fluorobenzoyl)ethyl]-4-(2-phenoxyphenyl)piperidine;
4-acetyl-1-allyl-4-[2-(4-chlorophenoxy)-5-fluorophenyl]piperidine;
4-ethylcarbonyl-4-[2-(4-fluorophenoxy)-4-methoxyphenyl]-1-dimethylallylpiperidine;
4-[5-bromo-2-(4-methylthiophenoxy)phenyl]-4-ethoxycarbonyl-1-dimethylallylpiperidine;
4-acetyl-1-allyl-4-[2-(4-bromophenoxy)-4,5-dichlorophenyl]piperidine;
1-allyl-4-4-ethylcarbonyl-4-[2-(4-trifluoromethylphenoxy)-5-methylthiophenyl]piperidine;
1-dimethylallyl-4-[2-(4-methoxyphenoxy)-5-trifluoromethyl]-piperidine-4-carboxylic acid;
1-acetyl-4-(2-phenoxyphenyl)piperidine-4-carbonyl bromide;
1-acetyl-4-(2-phenoxyphenyl)piperidine-4-carbonyl fluoride; and
1-(2-butynyl)-4-ethylcarbonyl-4-(2-phenoxyphenyl)-piperidine.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to be between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The compounds of the invention can be prepared according to one or more of the following methods in which R, R', X, Y and m, unless otherwise indicated, are as defined above.

METHOD A

A 2-phenoxyphenylacetonitrile of the formula

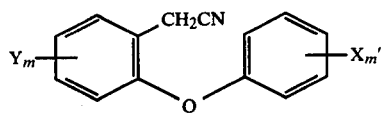
(I)

is subjected to bisalkylation with mechlorethamine hydrochloride in the presence of a strong base at a temperature ranging from ambient to about 85° C. to provide the corresponding 4-cyano-1-methyl-4-(2-phenoxyphenyl)piperidine of the formula

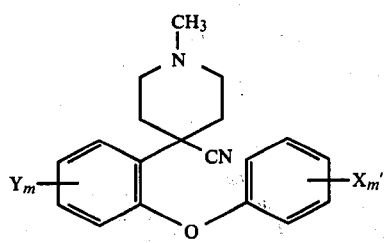
(II)

Preferred methods include the use of dimethylformamide or dimethylsulfoxide and sodium hydride as the strong base.

METHOD B

A compound of formula II is treated according to the first step of the von Braun reaction to provide the corresponding 1,4-dicyano-4-(2-phenoxyphenyl)piperidine of the formula

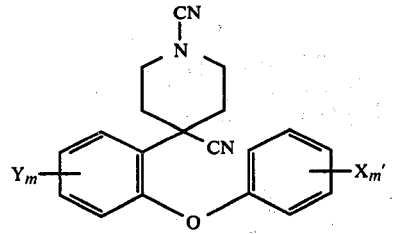
(III)

Also, a solvent such as chloroform or methylene dichloride, a mild acid scavenger such as potassium carbonate and a reaction temperature ranging from about ambient to reflux of the reaction mixture constitutes reaction conditions.

METHOD C

A compound of formula III is subjected to acid hydrolysis to provide the corresponding 4-(2-phenoxyphenyl)piperidine-4-carboxylic acid of the formula

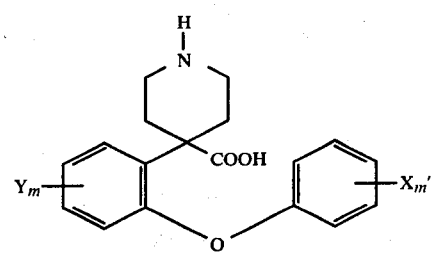
(IV)

A preferred method utilizes concentrated (48%) hydrobromic acid or a mixture of concentrated hydrobromic acid and glacial acetic acid at temperatures ranging from about 100° C. to reflux.

METHOD D

A compound of formula IV is acylated in the presence of an acid scavenging medium, a basic solvent or an acid scavenger, to provide the corresponding 1-alkanoyl-4-(2-phenoxyphenyl)piperidine-4-carboxylic acid of the formula

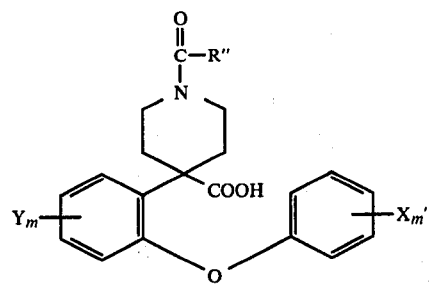
(V)

It is preferred method to utilize pyridine as an acid scavenging medium. Also, an appropriate alkanoyl halide, e.g., acetyl chloride, or an alkanoyl anhydride, e.g., acetic, can be the acylating agent.

METHOD E

A compound of formula V is carefully subjected to displacement with thionyl halide to provide the corresponding acid halide of the formula

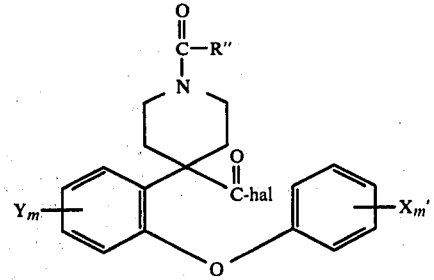
(VI)

A preferred method utilizes thionyl chloride with the displacement carried out by heating on a steam bath for about 5 minutes.

METHOD F

A compound of Formula II is treated with a Grignard reagent of the formula R"Mghal, in which R" is a straight or branched chain loweralkyl and hal is bromine or chlorine, under Grignard reaction conditions to provide the corresponding 4-(1-oxoalkyl)-4-(2-phenoxyphenyl)piperidine of the formula

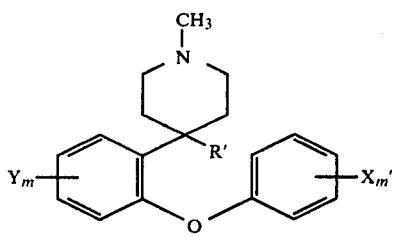

in which R' is loweralkanoyl. Preferred reaction conditions include a solvent such as ether or tetrahydrofuran and temperatures ranging from about 15° C. to reflux of the reaction mixture.

METHOD G

A compound of formula VII is treated according to the procedure of Method B to provide the corresponding N-cyano compound of the formula

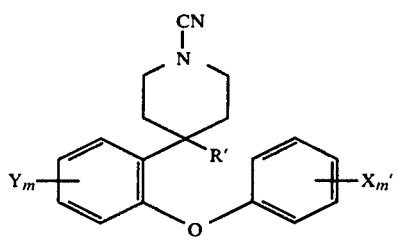

in which R' is loweralkanoyl.

METHOD H

A compound of formula III or VIII is subjected to hydrolysis to remove the N-cyano group to provide a compound of the formula

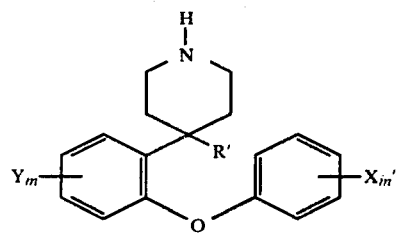

in which R' is cyano or loweralkanoyl. Preferred conditions include the use of a mild acid such as 2 N hydrochloric acid or a mixture of 2–3 N hydrochloric acid and glacial acetic acid and an elevated temperature ranging from about 90° C. to reflux of the reaction mixture.

METHOD I

A compound of formula VI is subjected to esterification by refluxing in the presence of an alcohol of the formula R"OH, in which R" is straight or branched chain alkyl, acid saturated to provide the corresponding 4-alkoxycarbonyl-4-(2-phenoxyphenyl)piperidine of the formula

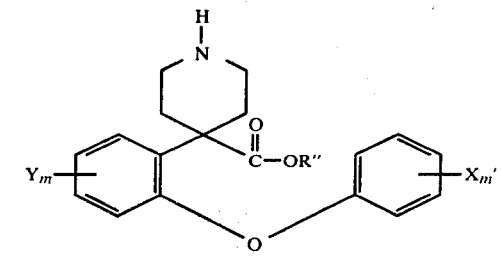

METHOD J

A compound of formula IX or X is alkylated with an appropriate alkylating agent by any convenient method known to the art to provide the corresponding N-substituted compound of the formula

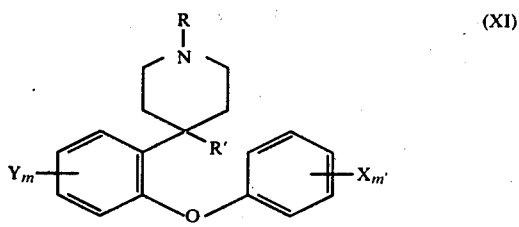

in which R is loweralkyl, loweralkenyl, loweralkynyl, tetrahydrofuryl methyl, cycloalkylloweralkyl, phenylloweralkyl or ethylene glycol ketal of the formula

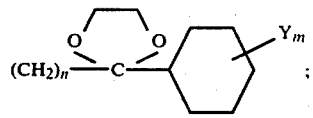

and R' is loweralkanoyl or loweralkoxycarbonyl. A preferred method includes the use of dimethylformamide as a solvent, sodium bicarbonate as an acid scavenger and a reaction temperature of from 50°–90° C. Optionally, a reaction initiator, preferably potassium iodide, may be used.

METHOD K

An ethylene ketal compound of formula XI is subjected to acid hydrolysis to provide the corresponding compound in which R is benzoylloweralkyl

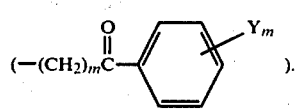

3 N hydrochloric acid in ethanol is preferred as the agent effecting hydrolysis.

METHOD L

A compound of formula XI in which R' is COOR" is hydrolyzed by any convenient method known to the art to provide the corresponding compound in which R' is COOH. The use of dilute sodium hydroxide is preferred.

METHOD M

A compound obtained in any of the above methods in which R is not H and R' is COOH is esterified by any convenient method known to the art to provide the corresponding compound in which R' is

loweralkyl. In a preferred method the acid precursor is converted to its acid halide which in turn is esterified.

In each of the above methods, optimum conditions depend upon starting materials, solvents, catalysts and other reaction components. This will become more apparent in the examples given below.

Starting materials depicted by formula I are either commercially available or can be prepared by routine methods according to the following sequence of reactions:

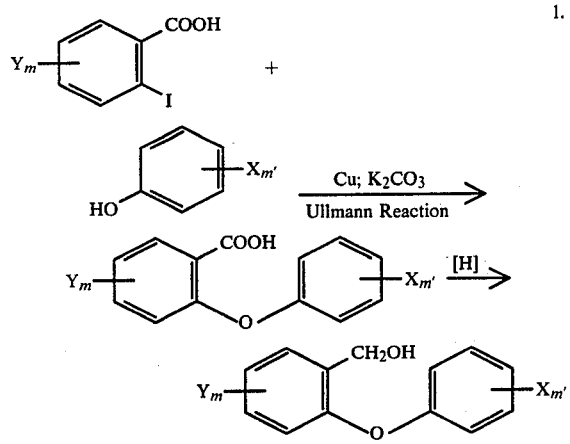

[reduction with sodium-bis-(2-methoxyethoxy)aluminum hydride (VITRIDE®)]

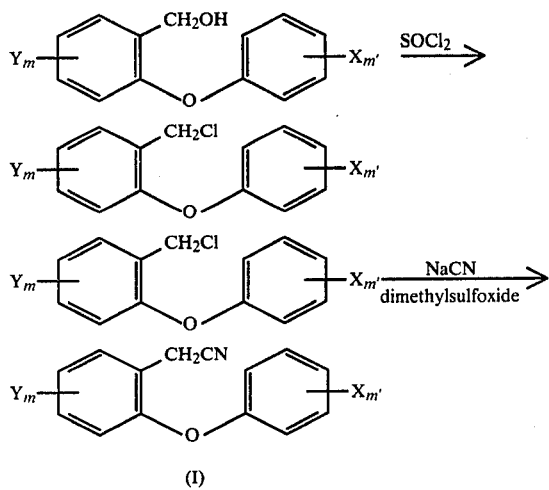

The invention is further illustrated by the following specific examples.

EXAMPLE 1

2.6 g of 99% sodium hydride are added portionwise to a solution of 4.4 g of 2-phenoxyphenylacetonitrile in 50 ml of dimethylformamide. The resulting reddish-brown mixture is stirred for 30 minutes before adding dropwise a solution of 4.0 g of mechlorethamine hydrochloride in 50 ml of dimethylformamide, maintaining gas evolution at a slow rate. After total addition, the mixture is stirred at 80°–85° C. for 15 hours. Thereafter, 100 g of ice are added before the mixture is extracted thrice with ether. The combined ether extracts are dried over potassium carbonate and then the solvent is removed under vacuum leaving a brownish oil. The oil is dissolved in a small amount of ether and passing through, with additional ether, an alumina column which is packed in ether. The effluent is concentrated leaving a heavy oil. The oil is converted to its hydrochloride which is recrystallized from an acetone-ether mixture leaving shiny prisms, mp 242°–244° C., of 4-cyano-1-methyl-4-(2-phenoxyphenyl)piperidine hydrochloride.

Analysis: Calculated for $C_{19}H_{20}N_2O \cdot HCl$: 69.41%C; 6.42%H; 8.52%N; 10.78%Cl. Found: 69.59%C; 6.57%H; 8.62%N; 10.90%Cl.

EXAMPLE 2

14.4 g of 97% sodium hydride are added in small portions with stirring to a mixture of 27.6 of 2-(4-chlorophenoxy)benzyl cyanide in 300 ml of dimethylformamide. After total addition, the mixture is stirred at ambient temperature for 45 minutes prior to adding dropwise 20.2 g of 98% mechlorethamine hydrochloride in 200 ml of dimethylformamide. Thereafter, the reaction mixture is stirred at 100° C. for 17 hours and permitted to cool. The cooled mixture is poured into 1000 g ice and then stirred. The aqueous mixture is extracted five times with 250 ml portions of ether. The combined ether extracts are extracted with 2 N hydrochloric acid and the combined acidic extracts are basified with a concentrated ammonium hydroxide solution providing an oil. The oil is extracted with three 250 ml portions of ether and the combined ether extracts are dried providing a dark crystalline material. The solid is chromatographed on an alumina column, ether eluant, to provide a white crystalline product, mp 99°–100.5° C., of 4-[2-(4-chlorophenoxyphenyl)]-4-cyano-1-methylpiperidine.

Analysis: Calculated for $C_{19}H_{19}ClN_2O$: 69.83%C; 5.86%H; 8.57%N; 10.85%Cl. Found: 69.92%C; 5.90%H; 8.70%N; 11.02%Cl.

EXAMPLE 3 a. A mixture of 147 g of iodobenzoic acid, 45.5 g of potassium carbonate in 57 ml of nitrobenzene is maintained with stirring at 160° C. for 40 minutes. Thereafter, 46.5 g of additional potassium carbonate which is followed by the addition of 73.1 g of 4-fluorophenol, another 46.5 g of potassium carbonate and 0.35 g of copper powder. The reaction mixture is stirred in a 160° C. bath for 45 minutes. The resulting solid is collected and then cooled to 0° C. before being mixed with 100 ml of water and 220 ml of 6 N hydrochloric acid. The aqueous mixture is then diluted to 1 l. total volume before being stirred with 450 ml of chloroform. The resulting white solid is collected and washed successively with chloroform and water. The solid is dissolved in hot acetone and the acetone solution is successively filtered and cooled to provide a white crystalline product. The product is recrystallized from acetone and then converted to a salt with potassium carbonate. The salt is dissolved in water and the aqueous solution acidified with 1 N hydrochloric acid to provide white crystals, mp 143°–146° C., of 2-(4-fluorophenoxy)benzoic acid.

b. 36.1 ml of 70% sodium-bis-(2-methoxyethoxy) aluminum hydride in benzene are added dropwise over a one hour span to a stirring mixture of 15 g of 2-(4-fluorophenoxy)benzoic acid in 150 ml of benzene under nitrogen at ambient temperature. After total addition, the reaction mixture is stirred for an additional 30 minutes and then permitted to stand for 4 days. Thereafter, the reaction mixture is cooled to 0° C. before adding 100 mls of 10% sodium hydroxide while stirring. Following this addition, the layers separate and the aqueous layer is extracted twice with 100 ml portions of benzene. The combined benzene solutions are successively washed twice with 100 ml portions of water, washed once with 60 ml of saturated sodium chloride solution and dried, providing a clear yellow oil. The oil is distilled at 118.5°–121.5° C. and 0.07 mm pressure to provide the clear, colorless liquid, 2-(4-fluorophenoxy)benzyl alcohol.

c. 8.5 g of thionyl chloride are added dropwise over a 10 minutes span to a stirring mixture of 13.0 g of 2-(4-fluorophenoxy)benzyl alcohol in 80 Ml of benzene at ambient temperature. After total addition, the reaction mixture is stirred for 16 hours before being carefully poured onto 350 ml of crushed ice containing 8 ml of sodium bicarbonate. The mixture is stirred until the ice melts. The layers separate and the benzene layer is successively washed twice with 40 ml portions of a half saturated sodium bicarbonate solution, washed twice with 40 ml portions of water, washed once with 25 ml saturated sodium chloride solution, dried and rotary evaporated to provide a clear liquid. The liquid is distilled at 106°–109° C. and 0.16 mm to provide a clear colorless liquid of 2-(4-fluorophenoxy)benzyl chloride.

d. 12.0 g of 2-(4-fluorophenoxy)benzyl chloride are added portionwise over a 30 minute span to a mixture of 2.9 g of sodium cyanide in 120 ml of dimethylsulfoxide. After total addition, the reaction mixture is stirred for 26 hours before being poured onto 150–200 ml of crushed ice. The mixture is extracted four times with 70 ml portions of ether and the combined ether extracts are successively washed four times with 50 ml portions of water, washed once with 25 ml of saturated sodium chloride solution and dried, providing a clear oil. The oil is distilled at 128.5° C. and 0.1 mm to provide 2-(4-fluorophenoxy)benzyl cyanide.

e. 2.3 g of 99% sodium hydride are slowly added to a mixture, under nitrogen, of 4.3 g of 2-(4-fluorophenoxy)benzyl cyanide in 30 ml of dimethylsulfoxide. After total addition, the mixture is stirred for an additional five minutes and then a mixture of 3.9 g of 95% mechlorethamine hydrochloride in 20 ml of dimethylsulfoxide is added portionwise over a 40 minutes span. After this addition, the reaction is stirred for 1 hour in a hot water bath at 70° C. and then permitted to stand at ambient temperature for 16 hours. The cooled reaction mixture is poured onto 150 ml of crushed ice and the diluted mixture is extracted thrice with 60 ml portions of ether. The combined ether extracts are successively washed with 25 ml of saturated sodium chloride solution and dried, providing a yellow solid. The solid is recrystallized from cyclohexane, leaving a white solid, mp 106°–107.5° C., of 4-cyano-4-[2-(4-fluorophenoxy)-phenyl]-1-methylpiperidine.

Analysis: Calculated for $C_{19}H_{19}FN_2O$: 73.52%C; 6.16%H; 9.03%N; 6.12%F. Found: 73.47%C; 6.04%H; 8.99%N; 6.23%F.

EXAMPLE 4

A solution of 2 g of 4-cyano-1-methyl-4-(2-phenoxyphenyl)piperidine, free base of Example 1, in 25 ml of ether is added dropwise with vigorous stirring to 5 ml of ethylmagnesium bromide. After total addition, stirring is continued for 16 hours. Thereafter, saturated aqueous ammonium chloride is added to decompose the reaction mixture. The ether solution is separated and then successively extracted thrice with 10 ml portions of 2 N hydrochloric acid, warmed on a steam bath and potassium carbonate is added. The resulting amine is dissolved in ether. The ether solution is dried and evaporated off. The resulting solid is purified by column chromatography (alumina column, 5% methanol in methylene chloride eluant). The purified product is converted, in ether, to its oxalic acid salt. The salt is recrystallized from a methyl alcohol-ether mixture to provide rhombic crystals, mp 180°–182° C., of 4-ethylcarbonyl-1-methyl-4-(2-phenoxyphenyl)piperidine oxalate.

Analysis: Calculated for $C_{21}H_{25}NO_2.C_2H_2O_4$: 66.79%C; 6.58%H; 3.39%N. Found: 66.64%C; 6.69%H; 3.41%N.

EXAMPLE 5

A solution of 2.5 g of 4-cyano-1-methyl-4-(2-phenoxyphenyl)piperidine, free base of Example 1, in 10 ml of tetrahydrofuran is added dropwise to 15 ml of methylmagnesium bromide in ether (2.5 M). After total addition, the reaction mixture is refluxed for 3 days and then decomposed with an excess of saturated ammonium chloride. The organic layer is separated and extracted four times with 10 ml portions of 2 N hydrochloric acid. The acidic solution is warmed on a steam bath for 1 hour before adding potassium carbonate. The resulting product is shaken into ether and the ethereal solution is evaporated to dryness, leaving a crude product. This product is purified by column chromatography (alumina column and a 5% methyl alcohol in methylene chloride eluant) and then converted, in ether, to its oxalic acid salt. The salt is recrystallized from an ethyl alcohol-ether mixture to give white prisms, mp 147°–149° C., of 4-acetyl-1-methyl-4-(2-phenoxyphenyl)piperidine oxalate.

Analysis: Calculated for $C_{20}H_{23}NO_2.C_2H_2O_4$: 66.14%C; 6.31%H; 3.50%N. Found: 66.16%C; 6.44%H; 3.27%N.

EXAMPLE 6

A solution of 2 g of 4-cyano-1-methyl-4-(2-phenoxyphenyl)piperidine, free base of Example 1, in 16 ml of tetrahydrofuran is added dropwise to a Grignard reagent prepared from 5.93 g of n-propyl iodide, 0.9 g of magnesium and 30 ml of ether. After total addition, the reaction mixture is stirred at reflux for 4 days. Thereafter, the mixture is decomposed with an excess of ammonium chloride followed by mild acid hydrolysis, providing a crude product. The product is purified by column chromatography (alumina column—a 5% methyl alcohol in methylene chloride mixture as eluant) and then converted, in ether, to its oxalic acid salt. The salt is recrystallized from a methyl alcohol-acetone-ether mixture to provide microgranules, mp 212°–213° C., of 1-methyl-4-propylcarbonyl-4-(2-phenoxyphenyl)piperidine oxalate.

Analysis: Calculated for $C_{22}H_{21}NO_2.C_2H_2O_4$ 67.41%C; 6.83%H; 3.28%N. Found: 67.24%C; 6.95%H; 3.33%N.

EXAMPLE 7

A solution of 6.8 g of 4-acetyl-1-methyl-4-(2-phenoxyphenyl)piperidine oxalate, Example 5, in 40 ml of chloroform is added dropwise to a rapidly stirring mixture of 14.7 g of potassium carbonate and 3.7 g of cyanogen bromide in 48.5 ml of chloroform. After total addition, the reaction mixture is successively stirred at reflux for 16 hours, filtered, washed five times with 100 ml portions of water, washed with 50 ml of saturated sodium chloride solution and dried, providing a crystalline material. The product is purified by chromatography (M 60 silica gel column, ether eluant) to provide a white solid, mp 121.5°-122° C., of 4-acetyl-1-cyano-4-[2-phenoxyphenyl]piperidine.

Analysis: Calculated for $C_{20}H_{20}N_2O_2$: 74.97%C; 6.29%H; 8.75%N. Found: 75.18%C; 6.31%H; 8.87%N.

EXAMPLE 8

A solution of 4.8 g of 4-acetyl-1-cyano-4-[2-phenoxyphenyl]piperidine, Example 7, in 50 ml of 2 N hydrochloric acid is refluxed for 16 hours, effecting a white precipitate. The precipitate is collected by filtration and then washed twice with 50 ml portions of water and dried, providing a white powder, mp 295° C., of 4-acetyl-4-(2-phenoxyphenyl)piperidine hydrochloride.

Analysis: Calculated for $C_{19}H_{22}ClNO_2$: 68.77%C; 6.68%H; 4.22%N; 10.68%Cl. Found: 68.73%C; 6.70%H; 4.41%N; 11.10%Cl.

EXAMPLE 9

A solution of 3.2 g of 1-methyl-4-ethylcarbonyl-4-(2-phenoxyphenyl)piperidine, free base of Example 4, in 30 ml of chloroform is added portionwise over a 10 minute span to a refluxing mixture of 7.5 g of potassium carbonate and 2.0 g of cyanogen bromide in 30 ml of chloroform. After total addition, stirring is continued at reflux for two additional hours. Thereafter, the mixture is filtered and the filtrate is concentrated to dryness, leaving an oil residue. The residue is taken up in about 50 ml of ethyl alcohol and the alcoholic solution is heated on a steam bath for 5–10 minutes before evaporating off the solvent. The resulting yellowish oil solidifies on standing and the solid is recrystallized from a benzene-hexane mixture to provide colorless crystals, mp 88°-89° C., of 1-cyano-4-ethylcarbonyl-4-(2-phenoxyphenyl)piperidine.

Analysis: Calculated for $C_{21}H_{22}N_2O_2$: 75.41%C; 6.63%H; 8.38%N. Found: 75.28%C; 6.80%H; 8.45%N.

EXAMPLE 10

A suspension of 2.8 g of 1-cyano-4-ethylcarbonyl-4-(2-phenoxyphenyl)piperidine, Example 9, in 30 ml of 2 N hydrochloric acid is stirred at reflux for 16 hours. The resulting crystalline product is successively collected by filtration, dried and recrystallized from a methyl alcohol-ether mixture to provide shiny plates, mp 296°-297° C. (dec), of 4-ethylcarbonyl-4-(2-phenoxyphenyl)piperidine hydrochloride.

Analysis: Calculated for $C_{20}H_{23}NO_2.CHl$: 69.44%C; 6.99%H; 4.05%N; 10.25%Cl. Found: 69.21%C; 6.94%H; 4.21%N; 10.29%Cl.

EXAMPLE 11

A mixture of 2.04 g of 4-ethylcarbonyl-4-(2-phenoxyphenyl)piperidine hydrochloride, Example 10, 1.3 g of β-bromoethylbenzene, 3 g of sodium bicarbonate and 2 g of potassium iodide in 15 ml of dimethylformamide is stirred at 70° C. for 16 hours. Thereafter, the mixture is permitted to cool before being diluted with 100 ml of water and 200 ml of ether. Layers separate and the ether solution is dried. The ether is evaporated off, leaving a brownish oil which is purified by column chromatography (alumina column, ether eluant). The purified pale yellowish oil is converted to a crystalline hydrobromic acid salt which recrystallized from an acetone-ether mixture to provide the product, mp 172°-175° C., of 4-ethylcarbonyl-1-phenethyl-4-(2-phenoxyphenyl)-piperidine hydrobromide.

Analysis: Calculated for $C_{28}H_{31}NO_2.HBr$: 68.04%C; 6.52%H; 2.83%N; 16.16%Br. Found: 68.21%C; 6.43%H; 2.76%N; 16.33%Br.

EXAMPLE 12

A solution of 2.6 g of 4-cyano-1-methyl-4-(2-phenoxyphenyl)piperidine, free base of Example 1, in 22 ml of chloroform is added rapidly to a stirred mixture of 1.5 g of cyanogen bromide and 6 g of potassium carbonate in 50 ml of chloroform. Thereafter, the reaction mixture is stirred at reflux for 16 hours and then filtered. The filtrate is concentrated to dryness, leaving an oily residue which is dissolved in a small volume of methyl alcohol in which it is warmed on a steam bath to decompose any unreacted cyanogen bromide. The methyl alcohol is then evaporated off, leaving a pale yellowish residue which solidifies with cooling. The solid is recrystallized from an acetone-hexane mixture to give rhombic crystals, mp 100°-101° C., of 1,4-dicyano-4-(2-phenoxyphenyl)piperidine.

Analysis: Calculated for $C_{19}H_{17}N_3O$: 75.21%C; 5.65%H; 13.85%N. Found: 75.14%C; 5.80%H; 14.09%N.

EXAMPLE 13

A suspension of 8 g of 1,4-dicyano-4-(2-phenoxyphenyl)piperidine, Example 12, in 120 ml of 48% hydrobromic acid is stirred at reflux for 16 hours. Thereafter, the excess is removed by distillation in vacuo, leaving a glassy residue. The residue is dissolved in 100 ml of water. The aqueous solution quickly becomes cloudy as crystals begin to deposit. The aqueous mixture is cooled at 0° C. for 16 hours before crystals are collected. The crystals are recrystallized from an ethyl alcohol-acetone-ether mixture to provide tannish prisms, mp 247°-249° C., of 4-(2-phenoxyphenyl)piperidine-4-carboxylic acid hydrobromide.

Analysis: Calculated for $C_{18}H_{19}NO_3.HBr$: 57.15%C; 5.33%H; 3.61%N; 21.12%Br. Found: 57.235C; 5.47%H; 3.68%N; 21.34%Br.

EXAMPLE 14

A mixture of 8 g of 4-(2-phenoxyphenyl)piperidine-4-carboxylic acid hydrobromide, Example 13, and 10 ml of acetic anhydride in 50 ml of pyridine is refluxed for 4 hours. Thereafter, the pyridine is removed by distillation in vacuo and the residue is triturated with 100 ml of 1 N hydrochloric acid. The oily residue is extracted thrice with portions of chloroform and the combined chloroform extracts are successively washed twice with water, dried, and concentrated, leaving a solid residue.

The residue is recrystallized from acetone to provide small prisms, mp 195°–197.5° C., of 1-acetyl-4-(2-phenoxyphenyl)piperidine-4-carboxylic acid.

Analysis: Calculated for $C_{20}H_{21}NO_4$: 70.77%C; 6.23%H; 4.18%N. Found: 70.98%C; 6.39%H; 4.04%N.

EXAMPLE 15

A suspension of 3.4 g of 1-acetyl-4-(2-phenoxyphenyl)piperidine-4-carboxylic acid, Example 14, in 5 ml of freshly distilled thionyl chloride is warmed on a steam bath for 5 minutes effecting a clear solution. The excess thionyl chloride is removed at 50° C. under reduced pressure leaving a yellowish solid. The solid is recrystallized five times from a benzene-cyclohexane mixture to provide the product, mp 106°–108° C., of 1-acetyl-4-(2-phenoxyphenyl)piperidine-4-carbonyl chloride.

Analysis: Calculated for $C_{20}H_{20}ClNO_3$: 67.12%C; 5.63%H; 3.91%N; 9.90%Cl. Found: 67.29%C; 5.64%H; 3.90%N; 9.92%Cl.

EXAMPLE 16

A mixture of 2 g of 1-acetyl-4-(2-phenoxyphenyl)-piperidine-4-carbonyl chloride, Example 15, in 50 ml of absolute ethyl alcohol saturated with anhydrous hydrogen chloride is stirred at reflux for 64 hours. Thereafter, the excess acid and alcohol is removed under reduced pressure, leaving a clear, glassy residue. The residue is dissolved in 30 ml of water and the aqueous solution is extracted with ethyl acetate. The aqueous solution is basified with potassium carbonate liberating an oil. The oil is dissolved in ether and the ethereal solution is dried before concentrating to dryness leaving a brownish oil. The oil, in ether, is converted to its oxalic acid salt which is recrystallized from a methyl alcohol-acetone-ether mixture to provide silky needles, mp 148°–150° C., of 4-ethoxycarbonyl-4-(2-phenoxyphenyl)piperidine oxalate.

Analysis: Calculated for $C_{20}H_{23}NO_3.C_2H_2O_4$: 63.60%C; 6.06%H; 3.37%N. Found: 64.02%C; 6.36%H; 3.32%N.

EXAMPLE 17

A mixture of 0.67 of 4-ethoxycarbonyl-4-(2-phenoxyphenyl)piperidine, free base of Example 16, 0.48 g of 2-bromoethylbenzene, 0.65 g of sodium bicarbonate and 0.65 g of potassium iodide in 15 ml of dimethylformamide is stirred at 60°–70° C. for 16 hours. Thereafter, the mixture is diluted with ether and the diluted mixture is filtered. The filtrate is concentrated in vacuo leaving a heavy reddish oil. The oil is purified by column chromatography (alumina column, ether eluant) to provide the pale yellowish oil which, in ether, is converted to its hydrobromic acid salt. The salt is recrystallized from an acetone-ether mixture to provide glistening plates, mp 178°–180° C., of 4-ethoxycarbonyl-1-phenethyl-4-(2-phenoxyphenyl)piperidine hydrobromide.

Analysis: Calculated for $C_{28}H_{31}NO_3 \cdot HBr$: 65.87%C; 6.29%H. 2.74%N. Found: 66.06%C; 6.28%H; 2.67%N.

EXAMPLE 18

A mixture of 1.8 g of 4-ethylcarbonyl-4-(2-phenoxyphenyl)piperidine, free base of Example 10, 0.7 g of chloromethylcyclopropane, 1.6 g of sodium bicarbonate and 1.6 g of potassium iodide in dimethylformamide is stirred at 80°–85° C. for 16 hours. Thereafter, the mixture is permitted to cool to ambient temperature before being diluted with 50 ml of water. The diluted mixture is extracted thrice with 30 ml portions of ether. The combined ether extracts are sequentially washed with 25 ml of a saturated sodium chloride solution, dried over magnesium sulfate for 1 hour and the solvent removed providing an oil. The oil is passed through an alumina absorption column packed in ether, elution with a solution of 10% methyl alcohol in ether provides the desired product which is converted to its oxalic acid salt. Recrystallization from acetone-ether provides a white powder, mp 206°–208° C., of 1-cyclopropylmethyl-4-ethylcarbonyl-4-(2-phenoxyphenyl)piperidine oxalate.

Analysis: Calculated for $C_{24}H_{29}NO_2.C_2O_2H_2$: 68.85%C; 6.89%H; 3.09%N. Found: 68.87%C; 6.89%H; 3.15%N.

EXAMPLE 19

A mixture of 1.4 g of 4-ethoxycarbonyl-4-(2-phenoxyphenyl)piperidine, free base of Example 16, 0.52 g of chloromethylcyclopropane, 1.2 g of sodium bicarbonate and 1.2 g of potassium iodide in 15 ml of dimethylformamide is stirred for 16 hours at 80°–85° C. Thereafter, the mixture is permitted to cool before being diluted with 100 ml of water and then 200 ml of ether. Layers separate and the ether solution is dried and then evaporated leaving a brownish oil. The oil is purified by chromatography (alumina column, ether eluant). The ether eluting solution is concentrated providing a colorless oil which, in ether, is converted to its hydrobromic acid salt. The salt is recrystallized from an acetone-ether mixture to provide granule crystals, mp 180°–182° C., of 1-cyclopropylmethyl-4-ethoxycarbonyl-4-(2-phenoxyphenyl)piperidine hydrobromide.

Analysis: Calculated for $C_{24}H_{29}NO_2.HBr$: 62.60%C; 6.56%H; 3.04%N; 17.35%Br. Found: 62.56%C; 6.69%H; 3.05%N; 17.56%Br.

EXAMPLE 20

A mixture of 2.5 g of 4-cyano-1-methyl-4-(2-phenoxyphenyl)piperidine, free base of Example 1, and 1.7 g of phenyl chloroformate in 50 ml of methylene chloride is permitted to stand for 24 hours before being poured onto 100 g of ice. Thereafter, the mixture is extracted with 50 ml of methylene chloride and the organic solution is successively washed twice with 50 ml portions of water, washed once with 40 ml saturated sodium bicarbonate solution, washed once with 40 ml saturated sodium chloride solution, dried and evaporated to provide an oil. The oil is chromatographed (silica gel 60 column, ether eluant) and then chromatographed (silica gel 60 column, ether-hexane (1:1) mixture eluant) until there is no indication of contamination by the layer chromatography. Thereafter, the product is chromatographed through the same absorbent, ether eluant to provide a glassy solid of 4-cyano-1-phenoxycarbonyl-4-(2-phenoxyphenyl)piperidine.

Analysis: Calculated for $C_{25}H_{22}N_2O_3$: 75.36%C; 5.57%H; 7.03%N. Found: 75.19%C; 5.68%H; 6.93%N.

EXAMPLE 21

A mixture of 1.8 g of 4-ethylcarbonyl-4-(2-phenoxyphenyl)piperidine, free base of Example 10, 0.93 g of 2-chloromethyltetrahydrofuran, 1.6 g of sodium bicarbonate and 1.6 g of potassium iodide in 20 ml of dimethylformamide is stirred at 80°–85° C. for 16 hours. Thereafter, the mixture is permitted to cool before being diluted with 50 ml of water. The diluted mixture is extracted four times with 30 ml portions of ether and the combined ether extracts are washed with 25 ml saturated sodium chloride solution and then dried, leaving an oil. The oil is chromatographed (alumina column, 10% methyl alcohol in ether eluant) to provide a purified oil which, in ether, is converted to its oxalic acid salt. The salt is successively washed well with ether and dried under vacuum, recrystallized from a methanol-acetone-ether mixture and washed with ether to provide a white solid, mp 149°–151° C., of 4-ethylcarbonyl-4-(2-phenoxyphenyl)-1-(2-tetrahydrofuranylmethyl)-piperidine oxalate.

Analysis: Calculated for $C_{27}H_{33}NO_7$: 67.05%C; 6.88%H; 2.90%N. Found: 67.19%C; 6.97%H; 2.91%N.

EXAMPLE 22

A mixture of 4-cyano-1-methyl-4-(2-phenoxyphenyl)-piperidine, free base of Example 1, in 15 ml of 48% hydrobromic acid is stirred at reflux for 16 hours. Thereafter, the excess acid is removed under reduced pressure, leaving a solid to which are added 10 ml of freshly distilled thionyl chloride. A clear solution results as the mixture is warmed on a steam bath. The excess thionyl chloride is distilled off, leaving a gummy residue which is dissolved in 50 ml of absolute ethyl alcohol. The alcoholic solution is stirred at reflux for 1 hour and then permitted to stand for 16 hours. Then, the ethyl alcohol and any excess acid is removed under reduced pressure. The residue is dissolved in water and the aqueous solution is basified with dilute ice cold sodium bicarbonate, liberating an amine which is dissolved in ether, The ethereal solution is dried before concentrating in vacuo, leaving a light brownish oil. The oil, in ether, is converted to its hydrobromic acid salt which is recrystallized from a methyl alcohol-acetone-ether mixture to give fine needles, mp 188°–180° C., of 4-ethoxycarbonyl-1-methyl-4-(2-phenoxyphenyl)piperidine hydrobromide.

Analysis: Calculated for $C_{21}H_{25}NO_3 \cdot HBr$: 60.00%C; 6.23%H; 3.33%N; 19.01%Br. Found: 59.77%C, 6.40%H; 3.29%N; 19.15%Br.

EXAMPLE 23

A solution of 14.9 g of 4-[2-(4-chlorophenoxyphenyl)]-4-cyano-1-methylpiperidine, Example 2, is added dropwise to a rapidly stirring mixture of 30.4 g of potassium carbonate and 7.6 g of cyanogen bromide in 80 ml of chloroform. After total addition, the reaction mixture is refluxed for 16 hours and then successively filtered, washed thrice with 150 ml portions of water, washed once with 50 ml saturated sodium chloride solution and dried to provide an oil. The oil is dissolved in chloroform and the chloroform solution is chromatographed (silica gel 60, ether as eluant) to provide a crystalline material. The material is recrystallized twice from acetone to give the product, mp 135°–136° C., of 4-[2-(4-chlorophenoxyphenyl)]-1,4-dicyanopiperidine.

Analysis: Calculated for $C_{19}H_{16}ClN_3O$: 67.55%C; 4.77%H; 12.44%N; 10.49%Cl. Found: 67.35%C; 4.63%H; 12.45%N; 10.43%Cl.

EXAMPLE 24

A mixture of 13.5 g of 4-[2-(4-chlorophenoxyphenyl)]-1,4-dicyanopiperidine, Example 23, in 250 ml of 48% hydrobromic acid is stirred at 120° C. for 16 hours and then refluxed for three additional hours. Thereafter, the mixture is permitted to cool to ambient temperature. The white precipitate is sequentially collected by filtration, washed several times with water and dried. The solid is washed again three times with 100 ml portions of water and then dried to give a white powder, mp>300° C., of 1-aminocarbonyl-4-[2-(4-chlorophenoxyphenyl)]piperidine-4-carboxylic acid.

Analysis: Calculated for $C_{19}H_{19}ClN_2O_4$: 60.88%C; 5.11%H; 6.48%N; 9.46%Cl. Found: 60.49%C; 5.24%H; 6.98%N; 9.52%Cl.

EXAMPLE 25

A mixture of 1.1 g of 4-[2-(4-chlorophenoxyphenyl)]-4-cyano-1-methylpiperidine, Example 2, in 25 ml of 48% hydrobromic acid is stirred at 130° C. for 16 hours. Thereafter, the reaction mixture is diluted with 175 ml of water before being rotary evaporated under reduced pressure at 85° C. The resulting glassy solid is dissolved in water and the aqueous solution chromatographed (Bio-Rad AG 50 W - X8 cation exchange resin column, 1.5–1.6 N ammonium hydroxide solution eluant) to provide a powdery white solid which is washed with water and then chloroform to give the product, mp 320° C., of 4-[2-(4-chlorophenoxyphenyl)]-1-methylpiperidine-4-carboxylic acid.

Analysis: Calculated for $C_{19}H_{20}ClNO_3$: 65.99%C; 5.83%H; 4.05%N; 10.25%Cl. Found: 65.80%C; 6.58%H; 3.93%N; 10.50%Cl.

EXAMPLE 26

A mixture of 1.8 g of 4-acetyl-4-(2-phenoxyphenyl)-piperidine, free base of Example 8, 0.75 g of 98% chloromethylcyclopropane, 1.7 g of sodium bicarbonate and 1.7 g of potassium iodide in 20 ml of dimethylformamide is stirred at 80°–85° C. for 16 hours. Thereafter, the mixture is cooled below ambient temperature before diluting with 50 ml of water. The aqueous solution is extracted four times with 30 ml portions of ether. The combined ether extracts are washed with 25 ml saturated sodium chloride solution and then dried to provide an oil. The oil is chromatographed (absorption alumina column, 10% methyl alcohol eluant) to provide a purified oil which is dissolved in ether and is converted to its oxalic salt, a white solid, mp 207.5°–208.5° C., of 4-acetyl-1-cyclopropylmethyl-4-(2-phenoxyphenyl)piperidine oxalate.

Analysis: Calculated for $C_{25}H_{29}NO_6$: 68.32%C; 6.65%H; 3.19%N. Found: 68.05%C; 6.73%H; 3.13%N.

EXAMPLE 27

A mixture of 4.4 g of 4-cyano-4-[2-(4-fluorophenoxy)-phenyl]-1-methylpiperidine, Example 3, in 95 ml of 48% hydrobromic acid is stirred at reflux for 16 hours. Thereafter, the mixture is diluted with 300 ml of water before being rotary evaporated at 80° C. to provide a tan solid. The solid is swirled with 300 ml of water and dissolved by raising the pH to 9 with concentrated ammonium hydroxide. The solution is permitted to stand for 96 hours. The pH is slowly lowered to 4 and then returned to 9 with concentrated ammonium hydroxide. The volume is reduced by rotary evaporation at 80° C. until a precipitate appears. Thereafter, the reaction mixture is cooled and the precipitate collected by filtration and then washed with water. The precipitate is sequentially washed with acetone, treated with 1 ml of 48% hydrobromic acid diluted 20 ml of water and applied to a Bio Rad A 650 W - X8 cation exchange resin, eluted with 5.8–8.7% ammonium hydroxide to provide a white powder, mp 284°–286° C., of 4-[2-(4-fluorophenoxyphenyl)]-1-methylpiperidine-4-carboxylic acid.

Analysis: Calculated for $C_{19}H_{20}FNO_3$: 69.28%C; 6.12%H; 4.25%N; 5.77%F. Found: 69.04%C; 5.98%H; 4.34%N; 5.63%F.

EXAMPLE 28

A mixture of 19.8 g of 4-cyano-4-[2-(4-fluorophenoxy)phenyl]-1-methylpiperidine, Example 3, in 200 ml of chloroform is added portionwise over a 15 minute span to a mixture of 33.4 g of 97% cyanogen bromide and 130 g of potassium carbonate in 250 ml of chloroform. After total addition, the mixture is successively refluxed for 16 hours, cooled, filtered, washed thrice with 300 ml portions of water and one 50 ml portion of saturated sodium chloride solution and dried, providing a clear, pale yellow oil which crystallizes on standing. The solid is dissolved in benzene, decolorized with charcoal and filtered through celite. It is then concentrated and rediluted with hexane, effecting a white crystalline powder, mp 107.5°-109.5° C., of 1,4-dicyano-4-[2-(4-fluorophenoxy)phenyl]piperidine.

Analysis: Calculated for $C_{19}H_{16}FN_2O$: 71.01%C; 5.02%H; 13.08%N. Found: 70.94%C; 4.83%H; 13.09%N.

EXAMPLE 29

A solution of 2.0 g of 1,4-dicyano-4-[2-(4-fluorophenoxy)phenyl]piperidine, Example 28, in 12 ml of glacial acetic acid and 21 ml of 3 N hydrochloric acid is stirred at 110°-120° C. for 18 hours. Thereafter, the solution is diluted with 50 ml of water and the diluted solution is rotary evaporated twice to near dryness. The residual material is diluted in 100 ml of water and 2 ml of 58% ammonium hydroxide, giving a milky solution at pH 9. This aqueous suspension is extracted thrice with 150 ml portions of a benzene-ether (1:1) mixture. The combined extracts are successively washed once with 50 ml water, once with 25 ml saturated sodium chloride and dried to provide a crystalline material. The material is recrystallized from a benzene-hexane mixture to provide fine white crystals, mp 126°-127° C., of 4-cyano-4-[2-(4-fluorophenoxy)phenyl]piperidine.

Analysis: Calculated for $C_{18}H_{17}FN_2O$: 72.95%C; 5.78%H; 9.46%N. Found: 73.18%C; 5.76%H; 9.34%N.

EXAMPLE 30

A mixture of 12.0 g of 1,4-dicyano-4-[2-(4-fluorophenoxy)phenyl]piperidine, Example 28, in 240 ml of 48% hydrobromic acid is stirred in a 150° C. bath for 40 hours before adding 120 ml of glacial acetic acid and continuing the stirring at the same temperature for 30 additional hours. Thereafter, the solution is permitted to stand for 64 hours before the excess is distilled off, leaving a paste-like residue. The residue is taken up in 50 ml of water and the aqueous mixture is rotary evaporated, leaving a solid which when washed with water and then ether becomes a tan-grey powder. The powder is decolorized in methanol (with charcoal) to give a white crystalline powder. The powder is recrystallized three times from a methyl alcohol-ether mixture to provide the product, melting range 180°-250° C. (dec), of 4-[2-(4-fluorophenoxy)phenyl]piperidine-4-carboxylic acid hydrobromide.

Analysis: Calculated for $C_{18}H_{18}FNO_3 \cdot HBr$: 54.56%C; 4.83%H; 3.54%N. Found: 54.55%C; 4.82%H; 3.67%N.

EXAMPLE 31

A mixture of 0.7 g of 4-[2-(4-fluorophenoxy)phenyl]-piperidine-4-carboxylic acid, Example 27, in 0.83 ml of acetic anhydride in 4.2 ml of pyridine is stirred at reflux for 4 hours. Thereafter, the excess pyridine is removed by rotary evaporation and the residue is taken up in 10 ml of water where it is treated with 10 ml of 1 N hydrochloric acid. The acidic mixture is extracted thrice with 20 ml portions of an ether-benzene (1:1) mixture and the combined extracts are successively washed twice with 40 ml portions of water, once with 15 ml saturated sodium chloride solution and dried to provide a glassy solid. The solid is recrystallized repeatedly from acetone-ether to provide a white crystalline powder, mp 192.5°-193.5° C., of 1-acetyl-4-[2-(4-fluorophenoxy)phenyl]piperidine-4-carboxylic acid.

Analysis: Calculated for $C_{20}H_{20}FNO_4$: 67.20%C; 5.64%H; 3.92%N Found: 67.13%C; 5.62%H; 3.60%N.

EXAMPLE 32

A mixture of 2.8 g of 4-ethoxycarbonyl-4-(2-phenoxyphenyl)piperidine, free base of Example 16, 1.2 g of allyl bromide, 2.5 g of sodium bicarbonate and a crystal of potassium iodide in 30 ml of dimethylformamide is stirred at 70°-80° C. for 16 hours. Thereafter, the mixture is diluted with water and ether, and the ether layer is separated and then dried. The ether is removed in vacuo, leaving a brownish oil which is purified by passing through an alumina column. Elution with ether provides a yellowish liquid which is converted in ether to its oxalic acid salt. The salt is recrystallized from a methyl alcohol-acetone-ether mixture to provide granules, mp 197°-199° C. (dec), of 1-allyl-4-ethoxycarbonyl-4-(2-phenoxyphenyl)piperidine oxalate.

Analysis: Calculated for $C_{23}H_{27}NO_3 \cdot C_2H_2O_4$: 65.92%C; 6.41%H; 3.07%N. Found: 65.58%C; 6.45%H; 2.95%N.

EXAMPLE 33

A mixture of 1.2 g of 4-[2-(4-chlorophenoxy)phenyl]-1,4-dicyanopiperidine, Example 23, and 15 ml of a glacial acetic acid-3 N hydrochloric acid (1:2) solution is stirred at 110° C. for 24 hours. Thereafter, the solution is diluted with 80 ml of water before being evaporated to dryness. The solid residue is made strongly basic with ammonium hydroxide and the alkaline solution is extracted with ether. The combined ether extracts are successively dried, filtered and concentrated to dryness, leaving a white solid. The solid is dissolved in methylene chloride and this solution is chromatographed (silica gel/methylene chloride column, 10% methyl alcohol in methylene chloride as eluant). The desired fractions are concentrated to dryness leaving an oil which solidifies on standing to a white granular material, mp 128°-130° C. This material, for purposes of obtaining an analytical sample, is recrystallized from cyclohexane to provide white needles of 4-[2-(4-chlorophenoxy)phenyl]-4-cyanopiperidine.

Analysis: Calculated for $C_{18}H_{17}ClN_2O$: 69.11%C; 5.48%H; 8.96%N. Found: 69.14%C; 5.54%H; 8.88%N.

EXAMPLE 34

A mixture of 1.5 g of 4-ethoxycarbonyl-4-(2-phenoxyphenyl)piperidine, Example 16, 1.4 g of γ-chloro-4-fluorobenzophenone ethylene ketal, 1.0 g of sodium bicarbonate and 1.5 g of potassium iodide in 15 ml of dimethylformamide is stirred at 70° C. for 16 hours.

Thereafter, the mixture is diluted with water and ether. The ether layer is separated and then dried before being concentrated in vacuo, leaving a brownish oil of 4-ethoxycarbonyl-1-[3-(4-fluorobenzoyl)propyl]-4-(2-phenoxyphenyl)piperidine ethylene glycol ketal. The oil is stirred with 15 ml of ethyl alcohol and 15 ml of 3 N hydrochloric acid for 3 hours. Thereafter, the solution is permitted to cool before being basified with sodium hydroxide followed by extraction with ether. The combined ethereal extracts are passed through an alumina column; elution with ether provides a purified oil. The oil, in ether, is converted to its oxalic acid salt which is recrystallized from an ethyl alcohol-ether mixture to provide microgranules, mp 178°–181° C., of 4-ethoxycarbonyl-1-[3-(4-fluorobenzoyl)propyl]-4-(2-phenoxyphenyl)piperidine oxalate.

Analysis: Calculated for $C_{30}H_{32}NO_4 \cdot C_2H_2O_4$: 66.30%C; 5.91%H; 2.41%N. Found: 66.03%C; 5.82%H; 2.38%N.

EXAMPLE 35

A mixture of 1.8 g of 4-ethylcarbonyl-4-(2-phenoxyphenyl)piperidine, free base of Example 10, 1.9 g of γ-chloro-4-fluorobutyrophenone ethylene ketal, 1.6 g of sodium bicarbonate and 1.6 g of potassium iodide in dimethylformamide is stirred at 80°–85° C. for 16 hours. Thereafter, the mixture is permitted to cool to ambient temperature, before being diluted with 50 ml of water followed by extraction with ether. The pH of the aqueous phase is adjusted to 9–10 with 40% sodium hydroxide and the basified mixture is sequentially stirred for three hours and extracted twice with 30 ml portions of ether. The combined ether extracts are washed with 25 ml of a saturated sodium chloride solution and then dried to provide an oil. The oil is stirred in a solution of 48 ml of absolute ethyl alcohol and 18 ml of 3 N hydrochloric acid for 21 hours. The pH of the alcoholic-acid solution is raised to 9–10 with 40% sodium hydroxide. The alkaline solution is extracted thrice with 30 ml portions of ether and the combined ether extracts are successively washed with 30 ml saturated sodium chloride solution, dried and evaporated leaving an oil. The oil is chromatographed (alumina column, 10% methyl alcohol in ether mixture as eluant) to provide an orange oil. The oil, in ether, is converted to its oxalic acid salt. The salt is recrystallized from a chloroform-ether mixture to provide a white powder, mp 221°–222.5° C. of 4-ethylcarbonyl-1-[3-(4-fluorobenzoyl)propyl]-4-(2-phenoxyphenyl)piperidine oxalate hemihydrate.

Analysis: Calculated for $C_{32}H_{34}FNO_7 \cdot \frac{1}{2}H_2O$: 67.11%C; 6.16%H; 2.44%N; 3.32%F. Found: 67.18%C; 6.03%H; 2.43%N; 3.15%F.

We claim:
1. A compound of the formula

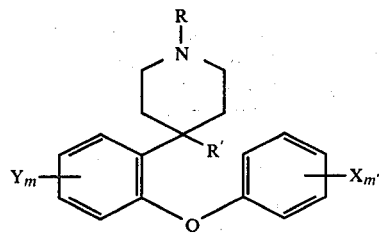

or a pharmaceutically acceptable acid addition salt thereof in which R is hydrogen, loweralkyl, loweralkenyl, loweralkynyl, cycloalkylloweralkyl, phenylloweralkyl, loweralkanoyl, phenoxycarbonyl, aminocarbonyl, benzoylloweralkyl, cyano, ethylene glycol ketal of the formula

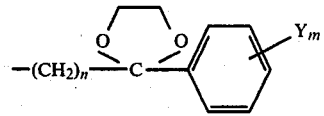

or tetrahydrofurylmethyl; R' is cyano, COOH, COZ, loweralkylcarbonyl or loweralkoxycarbonyl; X and Y are the same or different and each can be hydrogen, chlorine, fluorine, bromine, methoxy, methylthio or trifluoromethyl; Z is chlorine, fluorine or bromine; m and m' are the same or different and each can be the integer 1 or 2; and n is an integer of from 1 to 4, inclusive.

2. A compound as defined in claim 1 in which R is hydrogen, loweralkyl of from 1 to 3 carbon atoms, loweralkenyl of 3 or 4 carbon atoms, cycloalkylloweralkyl in which the cycloalkyl portion contains from 3 to 6, inclusive, carbon atoms and the loweralkyl portion contains from 1 to 3, inclusive, carbon atoms, phenylloweralkyl in which the loweralkyl portion contains from 1 to 3, inclusive, carbon atoms, benzoylloweralkyl in which the loweralkyl portion contains from 1 to 3, inclusive, carbon atoms, cyano, ethylene glycol ketal of the formula

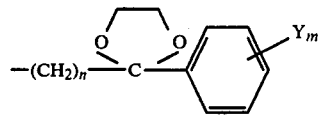

or tetrahydrofurylmethyl.

3. A compound defined in claim 2 in which X is hydrogen.
4. A compound defined in claim 2 in which Y is hydrogen, chlorine, fluorine or bromine.
5. A compound defined in claim 4 in which X is hydrogen.
6. A compound defined in claim 1 in which R' is cyano, COOH, COZ, loweralkylcarbonyl in which the loweralkyl portion contains from 1 to 3, inclusive, carbon atoms, loweralkoxycarbonyl in which the loweralkoxy portion contains from 1 to 3, inclusive, carbon atoms.
7. A compound defined in claim 6 in which X is hydrogen.
8. A compound defined in claim 6 in which Y is hydrogen, chlorine, fluorine or bromine.
9. A compound defined in claim 8 in which X is hydrogen.
10. A compound defined in claim 2 in which R' is cyano, COOH, COZ, loweralkanoyl in which the loweralkyl portion contains from 1 to 3, inclusive, carbon atoms, or loweralkoxycarbonyl in which the loweralkoxy portion contains from 1 to 3, inclusive, carbon atoms.
11. A compound defined in claim 10 in which X is hydrogen.
12. A compound defined in claim 10 in which Y is hydrogen, chlorine, fluorine or bromine.
13. A compound defined in claim 1 in which X is hydrogen.

14. A compound defined in claim 1 in which Y is hydrogen.

15. A compound defined in claim 1 in which Y is hydrogen, chlorine, fluorine or bromine.

16. A compound defined in claim 15 in which X is hydrogen.

17. The compound defined in claim 1 which is 4-cyano-1-methyl-4-(2-phenoxyphenyl)piperidine.

18. The compound defined in claim 1 which is 4-[2-(4-chlorophenoxyphenyl)]-4-cyano-1-methylpiperidine.

19. The compound defined in claim 1 which is 4-cyano-4-[2-(4-fluorophenoxy)phenyl]-1-methylpiperidine.

20. The compound defined in claim 1 which is 4-ethylcarbonyl-1-methyl-4-(2-phenoxyphenyl)piperidine.

21. The compound defined in claim 1 which is 4-acetyl-1-methyl-4-(2-phenoxyphenyl)piperidine.

22. The compound defined in claim 1 which is 1-methyl-4-propylcarbonyl-4-(2-phenoxyphenyl)piperidine.

23. The compound defined in claim 1 which is 4-acetyl-1-cyano-4-[2-phenoxyphenyl]piperidine.

24. The compound defined in claim 1 which is 4-acetyl-4-(2-phenoxyphenyl)piperidine.

25. The compound defined in claim 1 which is 1-cyano-4-ethylcarbonyl-4-(2-phenoxyphenyl)piperidine.

26. The compound defined in claim 1 which is 4-ethylcarbonyl-4-(2-phenoxyphenyl)piperidine.

27. The compound defined in claim 1 which is 4-ethylcarbonyl-1-phenethyl-4-(2-phenoxyphenyl)piperidine.

28. The compound defined in claim 1 which is 1,4-dicyano-4-(2-phenoxyphenyl)piperidine.

29. The compound defined in claim 1 which is 4-(2-phenoxyphenyl)piperidine-4-carboxylic acid.

30. The compound defined in claim 1 which is 1-acetyl-4-(2-phenoxyphenyl)piperidine-4-carboxylic acid.

31. The compound defined in claim 1 which is 1-acetyl-4-(2-phenoxyphenyl)piperidine-4-carbonyl chloride.

32. The compound defined in claim 1 which is 4-ethoxycarbonyl-4-(2-phenoxyphenyl)piperidine.

33. The compound defined in claim 1 which is 4-ethoxycarbonyl-1-phenethyl-4-(2-phenoxyphenyl)-piperidine.

34. The compound defined in claim 1 which is 1-cyclopropylmethyl-4-ethylcarbonyl-4-(2-phenoxyphenyl)piperidine.

35. The compound defined in claim 1 which is 1-cyclopropylmethyl-4-ethoxycarbonyl-4-(2-phenoxyphenyl)piperidine.

36. The compound defined in claim 1 which is 4-cyano-1-phenoxycarbonyl-4-(2-phenoxyphenyl)piperidine.

37. The compound defined in claim 1 which is 4-ethylcarbonyl-4-(2-phenoxyphenyl)-1-(2-tetrahydrofuranylmethyl)piperidine.

38. The compound defined in claim 1 which is 4-ethoxycarbonyl-1-methyl-4-(2-phenoxyphenyl)piperidine.

39. The compound defined in claim 1 which is 4-[2-(4-chlorophenoxyphenyl)]-1,4-dicyanopiperidine.

40. The compound defined in claim 1 which is 1-aminocarbonyl-4-[2-(4-chlorophenoxyphenyl)]piperidine-4-carboxylic acid.

41. The compound defined in claim 1 which is 4-[2-(4-chlorophenoxyphenyl)]-1-methylpiperidine-4-carboxylic acid.

42. The compound defined in claim 1 which is 4-acetyl-1-cyclopropylmethyl-4-(2-phenoxyphenyl)piperidine.

43. The compound defined in claim 1 which is 4-[2-(4-fluorophenoxyphenyl)]-1-methylpiperidine-4-carboxylic acid.

44. The compound defined in claim 1 which is, 1,4-dicyano-4-[2-(4-fluorophenoxy)phenyl]piperidine.

45. The compound defined in claim 1 which is 4-cyano-4-[2-(4-fluorophenoxy)phenyl]piperidine.

46. The compound defined in claim 1 which is 4-[2-(4-fluorophenoxy)phenyl]piperidine-4-carboxylic acid.

47. The compound defined in claim 1 which is 1-acetyl-4-[2-(4-fluorophenoxy)phenyl]piperidine-4-carboxylic acid.

48. The compound defined in claim 1 which is 1-allyl-4-ethoxycarbonyl-4-(2-phenoxyphenyl)piperidine.

49. The compound defined in claim 1 which is 4-[2-(4-chlorophenoxy)phenyl]-4-cyanopiperidine.

50. The compound defined in claim 1 which is 4-ethoxycarbonyl-1-[3-(4-fluorobenzoyl)propyl]-4-(2-phenoxyphenyl)piperidine ethylene glycol ketal.

51. The compound defined in claim 1 which is 4-ethoxycarbonyl-1-[3-(4-fluorobenzoyl)propyl]-4-(2-phenoxyphenyl)piperidine.

52. The compound defined in claim 1 which is 4-ethylcarbonyl-1-[3-(4-fluorobenzoyl)propyl]-4-(2-phenoxyphenyl)piperidine.

53. A method of treating pain in mammals which comprises administering to a patient an effective amount of a compound defined in claim 1.

54. A method of treating depression in mammals which comprises administering to a patient an effective amount of a compound defined in claim 1.

55. A method of treating convulsions in mammals which comprises administering to a patient an effective amount of a compound defined in claim 1.

56. A pharmaceutical composition for treating pain, depression or convulsions which comprises between 0.5 and 70% of a compound defined in claim 1 and a pharmaceutically acceptable carrier therefor.

57. A process for preparing a compound of the formula

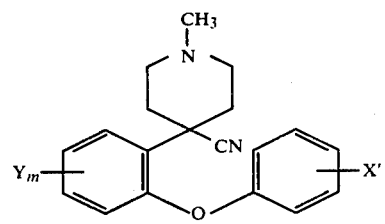

in which X and Y are the same or different and each can be hydrogen, chlorine, fluorine, bromine, methoxy, methylthio or trifluoromethyl and m and m' are the integer 1 or 2 which comprises treating a compound of the formula

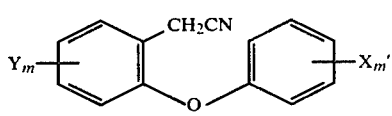

in which Y, X, m and m' are as defined earlier with mechlorethamine hydrochloride in the presence of a base at a temperature ranging from ambient to about 85° C.

58. A process for preparing a compound of the formula

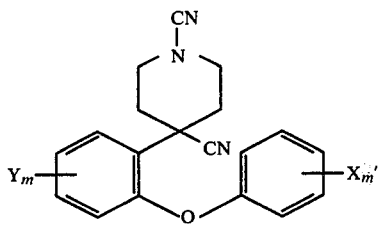

in which X and Y are the same or different and each can be hydrogen, chlorine, fluorine, bromine, methoxy, methylthio or trifluoromethyl and m and m' are the integer 1 or 2 which comprises treating a compound of the formula

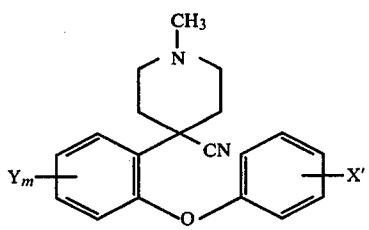

according to the first step of the von Braun reaction including a solvent such as chloroform or methylene chloride, a mild acid scavenger such as potassium carbonate and a reaction temperature ranging from about ambient to reflux as reaction conditions.

59. A process for preparing a compound of the formula

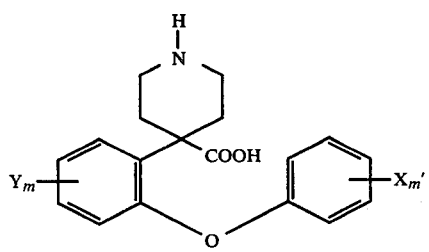

in which X and Y are the same or different and each can be hydrogen, chlorine, fluorine, bromine, methoxy, methylthio or trifluoromethyl and m and m' are the integer 1 or 2 which comprises subjecting to acid hydrolysis a compound of the formula

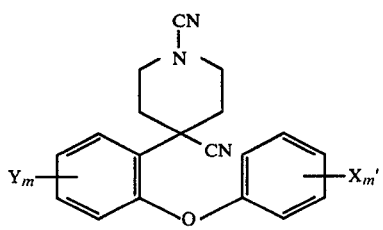

60. The process defined in claim 59 in which said hydrolysis is carried out with concentrated hydrobromic acid or a mixture of concentrated hydrobromic and glacial acetic acid at a temperature ranging from about 100° C. to reflux.

61. A process for preparing a compound of the formula

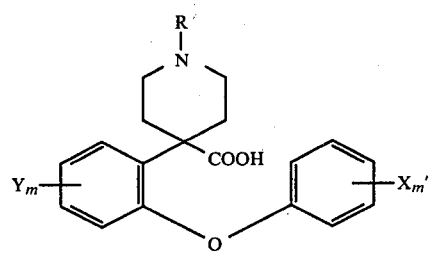

in which X and Y are the same or different and each can be hydrogen, chlorine, fluorine, bromine, methoxy, methylthio or trifluoromethyl and m and m' are the integer 1 or 2 and R is loweralkanoyl which comprises acylating a compound of the formula

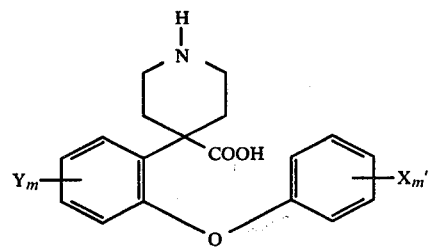

with an appropriate alkanoyl halide or alkanoylanhydride.

62. The process defined in claim 61 in which the acylation is carried out in the presence of pyridine.

63. A process for preparing a compound of the formula

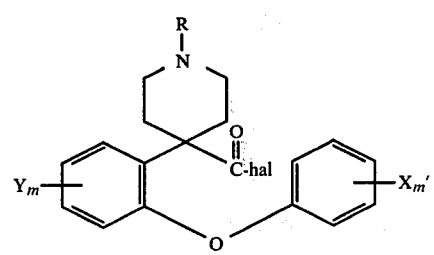

in which X and Y are the same or different and each can be hydrogen, chlorine, fluorine, bromine, methoxy, methylthio or trifluoromethyl; m and m' are the integer 1 or 2; and R is loweralkanoyl which comprises subjecting to displacement a compound of the formula

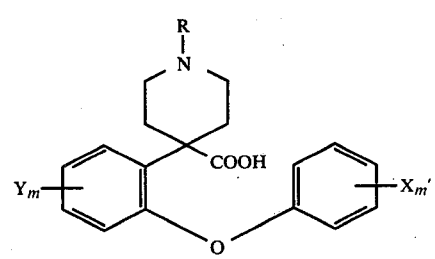

with an appropriate acid halide.

64. A process for preparing a compound of the formula

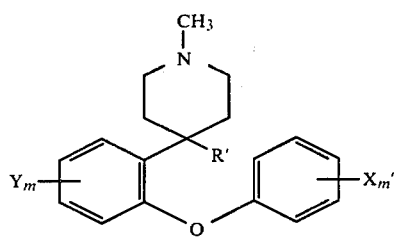

in which X and Y are the same or different and each can be hydrogen chlorine, fluorine, bromine, methoxy, methylthio or trifluoromethyl; m and m' are the integer 1 or 2; and R' is loweralkanoyl which comprises treating a compound of the formula

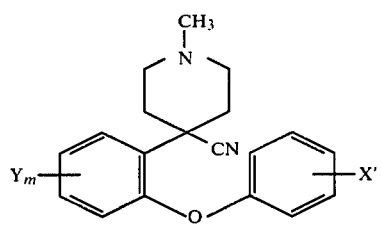

with a Grignard reagent of the formula R"Mghal in which R" is straight or branched chain loweralkyl and hal is bromine or chlorine under Grignard reaction conditions.

65. A process for preparing a compound of the formula

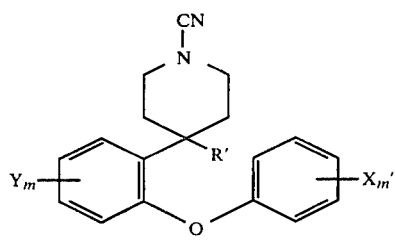

in which X and Y are the same or different and each can be hydrogen, chlorine, fluorine, bromine, methoxy, methylthio or trifluoromethyl; m and m' are the integer 1 or 2; and R' is loweralkanoyl which comprises treating a compound of the formula

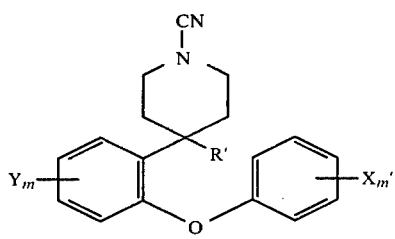

according to the first step of the von Braun reaction including a solvent such as chloroform or methylene chloride, a mild acid scavenger such as potassium carbonate and a reaction temperature ranging from about ambient to reflux as reaction conditions.

66. A process for preparing a compound of the formula

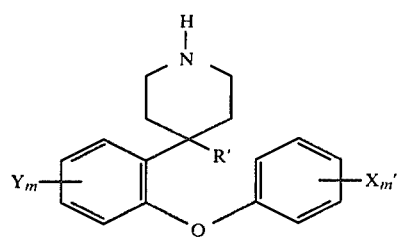

in which X and Y are the same or different and each can be hydrogen, chlorine, fluorine, bromine, methoxy, methylthio or trifluoromethyl; m and m' are the integer 1 or 2; R' is loweralkanoyl or CN which comprises subjecting to hydrolysis a compound of the formula

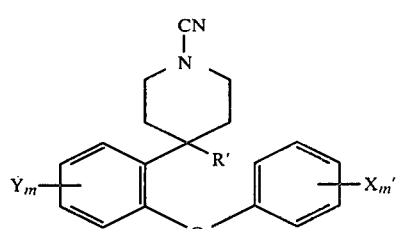

67. The process defined in claim 66 in which hydrolysis is carried out with a mild acid such as 2 N hydrochloric acid or a mixture of 2–3 N hydrochloric acid and glacial acetic acid and at a temperature ranging from about 90° C. to reflux.

68. A process for preparing a compound of the formula

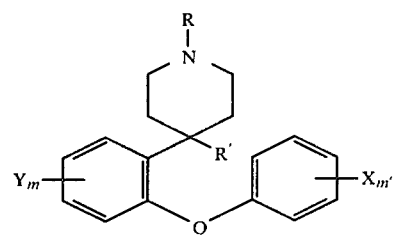

in which X and Y are the same or different and each can be hydrogen, chlorine, fluorine, bromine, methoxy, methylthio or trifluoromethyl; m and m' are the integer 1 or 2; R is hydrogen or CN; and R' is loweralkoxycarbonyl which comprises esterifying a compound of the formula

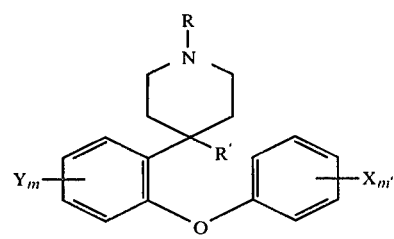

in which X, Y, m, m' and R are as defined earlier and R' is COZ in which Z is OH, chlorine, bromine or fluorine.

69. A process for preparing a compound of the formula

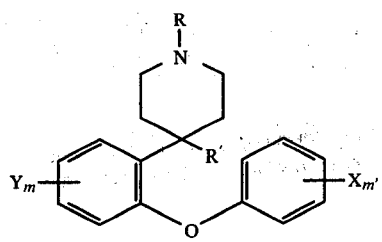

in which X and Y are the same or different and each can be hydrogen, chlorine, fluorine, bromine, methoxy, methylthio or trifluoromethyl; m and m' are the integer 1 or 2; R is loweralkyl, loweralkynyl, tetrahydrofurylmethyl, cycloalkylloweralkyl, phenylloweralkyl or ethylene glycol ketal of the formula

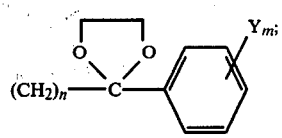

R' is loweralkanoyl or loweralkoxycarbonyl; and n is an integer between 1 and 4, inclusive, which comprises alkylating a compound of the formula

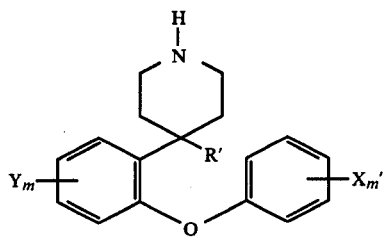

with an appropriate alkylating agent.

70. The process defined in claim 69 in which the alkylation is carried out in the presence of a solvent such as dimethylformamide, an acid scavenger such as sodium bicarbonate and at a reaction temperature of from about 50° to 90° C.

71. The process defined in claim 70 further comprising the use of a reaction initiator such as potassium iodide.

72. A process for preparing a compound of the formula

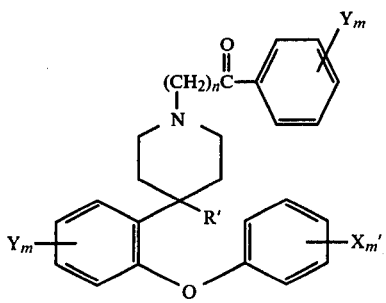

in which X and Y are the same or different and each can be hydrogen, chlorine, fluorine, bromine, methoxy, methylthio or trifluoromethyl; m and m' are the integer 1 or 2; and R' is loweralkanoyl or loweralkoxycarbonyl which comprises subjecting to acid hydrolysis a compound of the formula

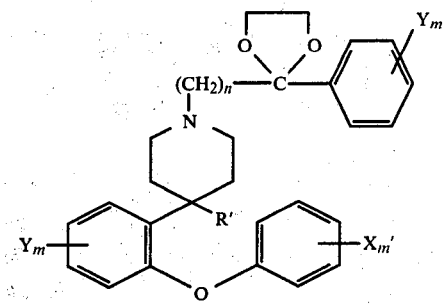

73. A process for preparing a compound of the formula

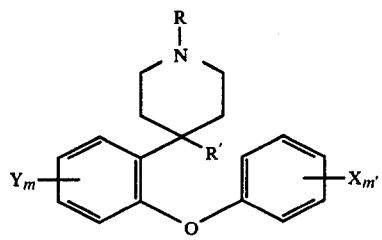

in which X and Y are the same or different and each can be hydrogen, chlorine, fluorine, bromine, methoxy, methylthio or trifluoromethyl; m and m' are the same or different and each can be the integer 1 or 2; R is hydrogen, loweralkyl, loweralkenyl, loweralkynyl, cycloalkylloweralkyl, phenylloweralkyl, loweralkanoyl, benzoylloweralkyl, cyano, ethylene glycol ketal of the formula

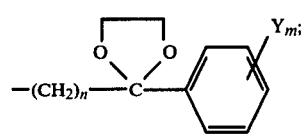

or tetrahydrofurylmethyl; and R' is loweralkanoyl or loweralkoxycarbonyl which comprises treating a compound of the formula

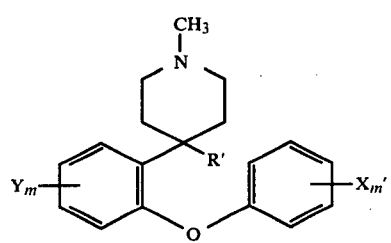

74. A process for preparing a compound of the formula

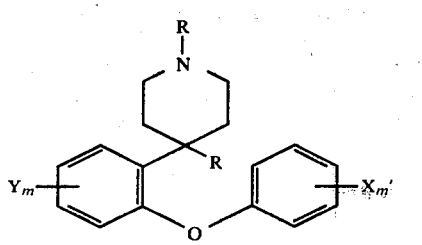

in which X and Y are the same or different and each can be hydrogen, chlorine, fluorine, bromine, methoxy, methylthio or trifluoromethyl; m and m' are the same or different and each can be the integer 1 or 2; R is loweralkyl, loweralkenyl, loweralkynyl, cycloalkylloweralkyl, phenylloweralkyl, loweralkylcarbonyl, benzoylloweralkyl, cyano, ethylene glycol ketal of the formula

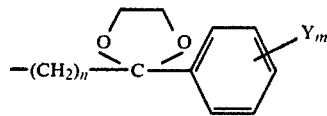

or tetrahydrofurylmethyl; and R' is COO loweralkyl which comprises esterifying a compound of the formula

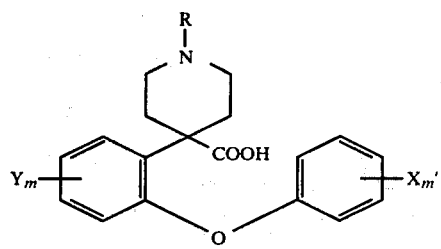

* * * * *

UNITED STATES PATENT AND TRADEMARK OFFICE
CERTIFICATE OF CORRECTION

PATENT NO. : 4,198,417
DATED : April 15, 1980
INVENTOR(S) : Ong et al.

It is certified that error appears in the above-identified patent and that said Letters Patent are hereby corrected as shown below:

Column 1, line 41, "ic" should be --is--;

Column 2, line 37, "date" should be --data--;

Column 10, line 11, "passing" should be --passed--;

Column 11, line 25, "Ml" should be --ml--;

Column 13, line 2, "...$H_2O_4O$" should be --$H_2O_4$:--;

Column 14, line 56, "57.235C" should be --57.23%C--;

Column 17, line 35, "188 - 180°C" should be --188 - 189°C--;

Column 20, line 43, "acid-3 N" should be --acid - 3N--; and

Column 27, line 26, in the structural formula, "X'" should be --Xm'--.

Signed and Sealed this

Twelfth Day of August 1980

[SEAL]

Attest:

Attesting Officer

SIDNEY A. DIAMOND
Commissioner of Patents and Trademarks